United States Patent
Besemer et al.

(10) Patent No.: US 6,849,156 B2
(45) Date of Patent: Feb. 1, 2005

(54) CATIONIC FIBERS

(76) Inventors: Arie Cornelis Besemer, Burg. Jhr. H. v.d. Boschstraat 111, NL-3958 CC Amerongen (NL); Anne Mieke Yvonne Wilhelmina Verwilligen, Laan van Vollenhove 479, NL-3706 CN Zeist (NL); Harm Jan Thiewes, Nico Bergsteynnweg 147, NL-3931 CC Woudenberg (NL); Dorine Lisa Van Brussel-Verraest, Kopeind 1, NL-2411 WG Bodegraven (NL)

(*) Notice: Subject to any disclaimer, the term of this patent is extended or adjusted under 35 U.S.C. 154(b) by 197 days.

(21) Appl. No.: 10/192,691

(22) Filed: Jul. 11, 2002

(65) Prior Publication Data
US 2003/0024662 A1 Feb. 6, 2003

Related U.S. Application Data
(60) Provisional application No. 60/304,111, filed on Jul. 11, 2001, and provisional application No. 60/341,856, filed on Dec. 21, 2001.

(51) Int. Cl.$^7$ .............................................. D21H 11/22
(52) U.S. Cl. ........................... 162/9; 162/146; 162/182; 8/116.1; 8/116.4; 8/181.1; 8/188; 8/196
(58) Field of Search .................. 162/9, 146, 182, 162/100; 8/116.1, 181.1, 188, 196, 116.4; 167/157.06

(56) References Cited

U.S. PATENT DOCUMENTS

| 3,364,200 | A | | 1/1968 | Ashton et al. |
| 4,001,032 | A | | 1/1977 | Heath et al. |
| 4,505,775 | A | | 3/1985 | Harding et al. |
| 6,368,456 | B1 | * | 4/2002 | Cimecioglu et al. ........ 162/146 |
| 6,379,494 | B1 | * | 4/2002 | Jewell et al. .................. 162/9 |

FOREIGN PATENT DOCUMENTS

| NL | 9301172 | 2/1995 |
| WO | 97/36037 A2 | 10/1997 |
| WO | 97/36052 A2 | 10/1997 |
| WO | 99/34055 A1 | 7/1999 |
| WO | 00/26257 A1 | 5/2000 |
| WO | 00/50462 A1 | 8/2000 |
| WO | 00/50463 A1 | 8/2000 |
| WO | 01/00681 A1 | 1/2001 |
| WO | 01/34656 A1 | 5/2001 |
| WO | 01/34657 A1 | 5/2001 |
| WO | 01/48025 A1 | 7/2001 |
| WO | 01/83887 A1 | 11/2001 |

OTHER PUBLICATIONS

Patent Abstracts of Japan, vol. 2000, No. 01, Jan. 31, 2000, JP 11 279206 A (SNC:KK; Sakairi Nobuo), Oct. 12, 1999.

(List continued on next page.)

Primary Examiner—Peter Chin
(74) Attorney, Agent, or Firm—Burns, Doane, Swecker & Mathis, L.L.P.

(57) ABSTRACT

A cationic cellulosic fibre containing between 1 and 30 cationic groups and between 0.1 and 20 aldehyde groups per 100 anhydroglucose units is a suitable basis for producing paper and tissue products without the necessity of using non-biodegradable cationic polymers as wet strength additives. The cationic cellulosic fibre can be obtained by oxidation of the fibre to introduce aldehyde groups, followed by reaction of part of the aldehyde groups with a nitrogen-containing reagent such as betaine hydrazide hydrochloride. The fibre is advantageously combined with an anionic polymer such as monoaldehyde carboxyl-starch or with anionic cyclodextrin.

14 Claims, 1 Drawing Sheet

OTHER PUBLICATIONS

Denter, U . . . et al., "Verfahrenstechnische Methoden zur permanenten Fixierung von Cyclodextrinderivaten auf textilen Oberflaechen," Textilveredlung, 1997 pp. 33–39, vol. 32, No. 1/2.

Denter, U., et al., "Surface Modification of Synthetic and Natural Fibres by Fixation of Cyclodextrin Derivatives," Journal of Inclusion Phenomena and Molecular Recognition in Chemistry, 1996, pp. 197–202, vol. 25.

Espy, Herbert H., "The Mechanism of Wet–Strength Development in Paper: a Review," Tapi Journal, Apr. 1995, pp. 90–99, vol. 78, No. 4.

Gruber, E., et al., "Cationization of Cellulose Fibers in View of Applications in the Paper Industry," Cellulose Derivatives, Modification, Characterization and Nanostructures, Ed. T. H. Heinze W. G. Glasser, A.C.S., Washington, D.C., 1998, pp. 94–106.

* cited by examiner

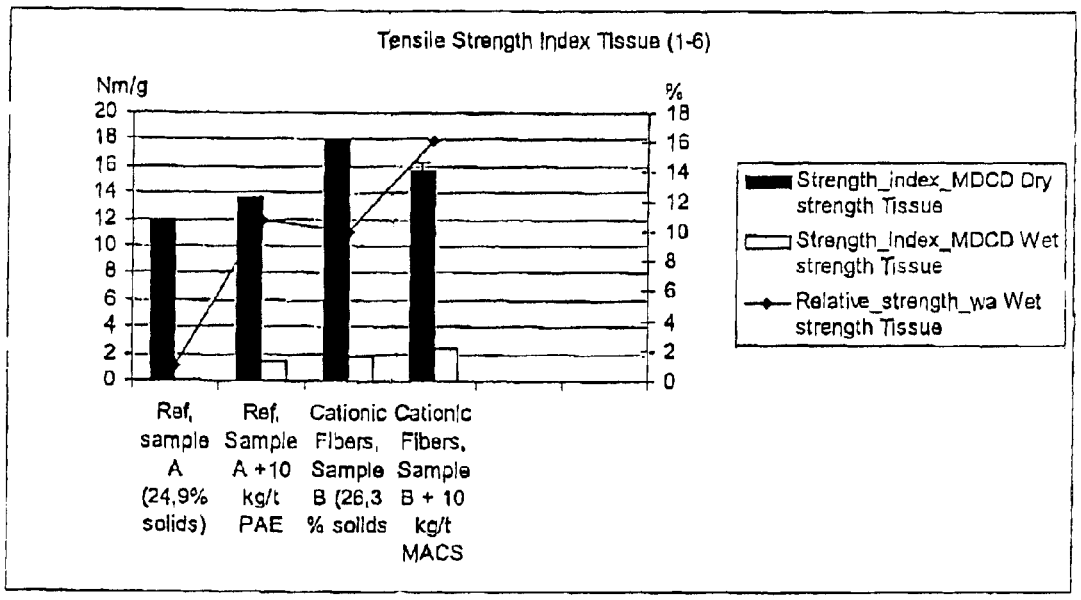
FIG. 1
FIG. 2
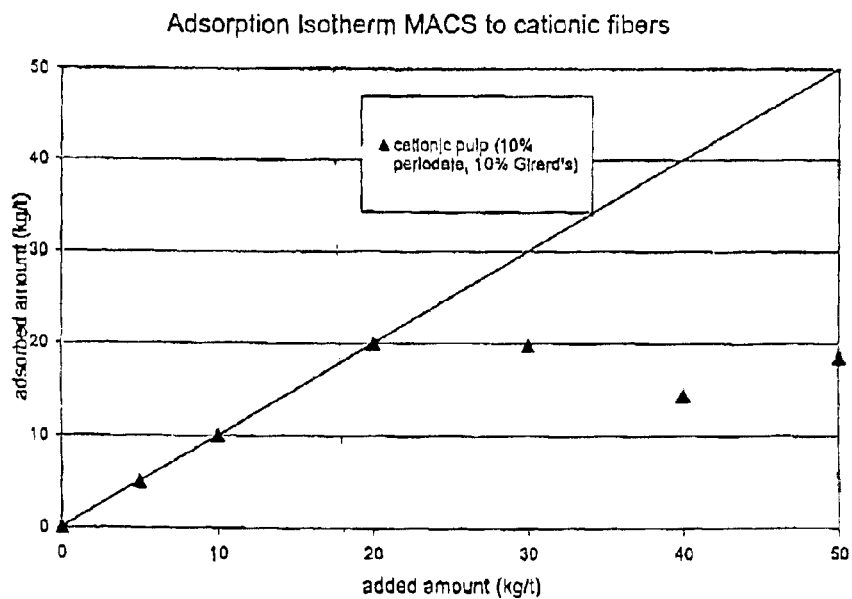

CATIONIC FIBERS

This application claims priority under 35 U.S.C. § 119 to U.S. Provisional Application Nos. 60/304,111 entitled COUPLING OF MODIFIED CYCLODEXTRINS TO FIBERS and filed on Jul. 11, 2001 and 60/341,856 entitled CATIONIC FIBRES and filed on Dec. 21, 2001, the entire contents of which are hereby incorporated by reference.

The present invention relates to novel cationic fibres and to fibrous products having improved strength containing such cationic fibres and optionally an anionic wet strength agent. The invention furthermore relates to a process of producing a cationic fibre.

BACKGROUND

Wet strength is an important characteristic of paper and tissue products, and in non-woven products. Wet strength of such products can be increased by using wet strength additives. The most widely used wet strength additives for the paper industry are melamine-formaldehyde resins, urea-formaldehyde resins and poly(amino)amide epichlorohydrin, PAE (see Espy, TAPPI Journal, 78, 90 (1995)). There is a tendency, however, to move away from such oil-based chemicals, because they are not renewable and have a poor biodegradability. The use of PAE is under pressure for several reasons: high price of PAE itself, poor repulpability and biodegradability of the paper product, and presence of toxic monomers and residues in the wet strength resin. The use of PAE could be avoided by providing cationic charge in the fibre itself and adding carboxylated or oxidized carbohydrates to these fibres. These carbohydrates have the desired renewability and degradability and are capable of providing wet strength to paper products; see WO 01/83887.

Cationic cellulosic fibre is a known product. U.S. Pat. No. 4,505,775 discloses a cationic cellulose obtained by reaction of cellulose fibre with a condensate of epichlorohydrin and dimethylamine. The cationic fibre has improved dye retention characteristics. A more recent survey of cationic cellulose fibres by Gruber et al. in *Cellulose Derivatives, Modification, Characterisation and Nanostructures*, Ed. T. J. Heinze and W. G. Glasser, A.C.S., Washington D.C., 1998, pp. 94–106, shows that the current cationisation of fibres still uses epichlorohydrin-type reactions. Therefore, the currently known cationic fibres do not provide a satisfactory solution to the problem of providing paper and non-woven products with sufficient wet strength based on renewable and biodegradable materials.

SUMMARY OF THE INVENTION

A novel class of cationic fibres was found, which has the advantageous feature that, in addition to cationic groups such, as triakylammonium groups, aldehyde groups are present in a varying, and adjustable amount. These aldehyde groups enhance the binding power of the fibre and are suitable for introducing additional functionality into the fibre. Thus, the invention concerns bifunctional cationic cellulosic fibres containing cationic groups and aldehyde groups in the same molecule. The invention also pertains to a process for producing these cationic fibres. Furthermore, the invention pertains to paper, tissue and non-woven products as well as to absorbent articles containing the cationic fibres.

BRIEF DESCRIPTION OF THE DRAWINGS

FIG. 1 shows a comparison between the wet strength of tissue paper containing cationic fibers treated with a negatively charged wet strength agent (MACS) and tissue paper containing a non-treated fiber and PAE.

FIG. 2 shows the adsorption isotherm MACS to cationic fibers.

DESCRIPTION OF THE INVENTION

The invention provides functional analogues of cationic fibres. The fibres can be fibres from chemical pulp, mechanical pulp, thermo-mechanical pulp, chemo-mechanical pulp, chemo-thermo-mechanical pulp (CTMP) and/or recycled fibres. The fibres may also comprise regenerated cellulosic fibres, such as lyocell, viscose and/or rayon.

The fibre or fibrous carrier, e.g. paper and paper products, tissues and the like, is positively charged (cationic derivatisation) by amino- or azido-alkylation, or oxidation to introduce aldehyde functions followed by reaction with amines or other nitrogen-containing reagents. The cationic derivatisation is performed to an extent that allows sufficient coupling of opposite charges, depending on the particular use of the coupling product. In general, a degree of ionisation of 0.1–50 ionic charges per 100 monomer units of the carrier, preferably from 1 to 20 charges per 100 units.

Thus, the cationic fibre according to the invention is a cellulosic material containing at least 0.1 cationic group, up to e.g. 50 cationic groups per 100 anhydroglucose unit (AGU). In particular the fibre contains between 1 and 30 cationic groups, more in particular between 2 and 10 cationic groups per 100 AGU. The cationic groups may be any charged groups, wherein the charge may be acid-independent, such as in trisubstituted ammonium, trisubstituted phosphonium and disubstituted sulphonium groups, wherein the substituents may be alkyl, alkenyl, aryl and their substituted analogues such as hydroxyalkyl, ammonioalkyl, alkylaryl, arylalkyl, and their cyclic analogues such as in N-pyridylium. Instead, the charge may be acid-dependent such as in amino, and mono- and disubstituted amino groups. Examples of acid-independent charged groups include trimethylammonio, triethylammonio, N,N-dimethylhydroxyethylammonio, N,N-dimethylbenzylammonio, 1-methyl-1-piperidinio, 1-pyridinio, tributylphosphonio, triphenylphosphonio, dimethylsulphonios and the like. Examples of acid-dependent charged groups include amino, ethylamino, dimethylamino, pyrrolidino, morpholino, and the like. The preferred charged group is trimethylammonio $(CH_3)_3N^+$—.

The cationic cellulosic fibre contains at least 0.05, up to 50 aldehyde groups per 100 anhydroglucose units. Preferably, the proportion of aldehyde groups is between 0.1 and 20 per 100 AGU, most preferably between 0.5 and 10 aldehyde groups per 100 AGU. Typically, the aldehyde groups result from the oxidation of hydroxymethyl (—$CH_2OH$) or hydroxymethylene (—CHOH—) groups of the carbohydrate, but they may also be the result of other modifications, such as the introduction of alkene functions, e.g. by reaction of the cellulose with butadiene-monoepoxide or with tetrahydrophthalic acid (see WO 97/36037) followed by ozonolysis. Also, fibres also containing hemicellulose with galactose and mannose units can be ozonolysed to introduce aldehyde functions (see WO 97/36052). In addition to the aldehyde groups, the cationic fibre according to the invention may contain carboxylic groups, especially between 0.1 and 20 carboxylic groups per 100 AGU. These can result from partial oxidation of aldehyde groups, e.g. by nitroxyl-mediated oxidation of hydroxymethyl groups. The ratio between cationic groups and aldehyde groups is between 1:100 and 1000:1, preferably between 1:10 and 1000:1, more preferably between 1:2 and 100:1.

The cationic cellulosic fibre can be prepared by first introducing aldehyde groups. A first, convenient method of introducing aldehyde groups consists of oxidation of dihydroxyethylene groups —CHOH—CHOH—, i.e. the 2,3-positions of the cellulosic AGU, using periodate ($MIO_4$ or $M_5IO_6$, wherein M is e.g. hydrogen or an alkali metal or alkaline earth metal) or similar oxidising agents, resulting in two aldehyde groups. Another useful method involves oxidation of hydroxymethyl groups —$CH_2OH$, i.e. the 6-position of the AGU, using nitric oxides, in particular nitroxyl-mediated ("TEMPO") oxidation using hypochlorite, hydrogen peroxide, peracids such as peroxosulphuric acid, or oxygen as reoxidators, optionally using metal compounds, metal complexes or redox enzymes as cocatalysts. These oxidations have been described in U.S. Pat. No. 3,364,200, NL 9301172, WO 00/50462, WO 00/50463, WO 01/34657 and WO 01/00681, for example. The aldehydes can also be introduced by a combination of oxidation methods, e.g. TEMPO-mediated oxidation followed by periodate oxidation, resulting in aldehydes at positions 2, 3 and 6 of the AGU (see WO 01/34656).

The aldehyde-functionalized fibre can conveniently be reacted with an agent having both an unsubstituted amino group (—$NH_2$) for coupling with the aldehyde function, and a cationic group, such as a trialkylammonio group, or a potentially cationic groups such as an amino group, preferably a tertiary amino group (e.g. $N^3,N^3$-dimethyl-1,3-propane-diamine). The amino group can be present on an aliphatic (alkyl) position, e.g. as —$CH_2NH_2$, which upon condensation with the aldehyde function (O=CH—) results in an imine (—$CH_2$N=CH—), which is then preferably stabilized by reduction to an amine (—$CH_2$NH—$CH_2$—), e.g. by borohydride reduction, dithionite reduction, or metal-catalysed hydrogenation. Preferably, however, the starting amino group is stabilized, e.g. as a hydrazine (—NH—$NH_2$), a carboxamide (—CO—$NH_2$), a sulphonamide (—$SO_2$—$NH_2$) or the like, especially a hydrazide (—CO—NH—$NH_2$) or sulphohydrazide (—$SO_2$—NH—$NH_2$), resulting, upon reaction with the aldehyde, in stable coupling, e.g. as a hydrazone (—CO—NH—N=CH—). Very suitable reagents are Girard's reagents T, trimethylammonioacetic hydrazide (($CH_3)_3N^+CH_2$CONHNH$_2$; betaine hydrazide hydrochloride) and P, pyridinioacetic hydrazide. The reaction of Girard's reagents with carbohydrates is known per se, from U.S. Pat. No. 4,001,032.

The reaction with the stabilized amine reagent such as Girard's reagent can be performed by treatment with 1–30 wt. % of reagent with respect to the fibre dry weight to a suspension (0.5–5 wt. %, especially 1–2 wt. %) of the aldehyde-functionalized fibre in water. The pH is usually between 2 and 7, in particular between 4 and 5, the reaction time is typically from 2 minutes to two hours and the temperature is between 20 and 100° C., especially between 36 and 90° C. The fibres are then washed with water to remove excess reagent.

As an alternative, the cationic, aldehyde-functionalized fibres can be obtained by first cationising the fibres, and then introducing aldehyde functions by one of the methods mentioned above. Thus, the fibres may be cationized by reaction with a cationising agent, such as 2-chloroethyltrimethylammonium, 3chloro-2-hydroxypropyltrimethylammonium, or glycidyl trimethylammonium chloride or other epoxide reactants having cationic functions, and then be subjected to periodate oxidation or TEMPO-mediated oxidation.

The cationic fibre containing aldehyde functions can be used as wet-strong paper itself, or be used for binding anionic functionalities, such as wet strength additives, dry strength additives, anionic dyes and the like. An example of a suitable dry strength additive is carboxymethyl cellulose. An example of an anionic dye includes Congo red. Other anionic functionalities comprise oxidized cyclodextrins capable of inclusion of odorous and other components.

Suitable wet strength additives are anionic polymers, especially biopolymers. Examples thereof are carbohydrates having aldehyde functions together with carboxyl functions, wherein the carboxylic groups provide the necessary negative charge, and the aldehyde functions provide for binding with the fibre. These can be starch, dextrin, cyclodextrin, guar and similar carbohydrate derivatives, wherein a part of the hydroxyl functions are oxidized to aldehyde groups, and a part thereof is further oxidized to carboxylic groups. Suitable examples of anionic polymers to be used according to the invention include so-called MACS, i.e. dialdehyde starch partially further oxidized to monoaldehyde-monocarboxyl starch; this product and its preparation are described in WO 00/26257. The use of MACS and other anionic aldehyde-containing polymers as wet strength agents is described in WO 01/83887.

The aldehyde-containing anionic polymers can be combined, usually as aqueous solutions or dispersions, with the cationic cellulosic fibres of the invention in a manner known for the application of wet strength agents. The amount of anionic agent is preferably between 0.1 and 10% by weight, especially between 0.2 and 4% by weight, with respect to the cellulosic fibre. Further alternate layering with aldehyde-containing anionic polymer and a cationic polymer can also be advantageous.

Anionic charges can be introduced onto cyclodextrin molecules in a manner known per se. Suitable methods therefore include oxidation of cyclodextrin with e.g. periodate, followed by chlorite, or by direct oxidation with hypochlorite, resulting in one or more glucose units being opened to dicarboxy-oxabutyleneoxy [—O—CH(COOH)—CH(CH$_2$OH)—O—CH(COOH)—] units, or with periodate, followed by oxidation with peracetic acid and bromine, as described in WO 00/26257, resulting in similar ring-opened units with both aldehyde and carboxyl groups.

Preferably however, the oxidation is focussed on the 6-hydroxymethyl groups, using hypoclorite or persulphuric acid and nitroxyl-mediation, e.g. using TEMPO or 4-acetamido-TEMPO, as mentioned above. The resulting DS for anionic charges is preferably between 0.1 and 0.3, more preferably 0.17–0.25 for α-cyclodextrins, 0.14–0.22 for β-cyclodextrins, and 0.12–0.2 for γ- and higher cyclodextrins.

The fibres thus prepared can be used for making paper, tissues or non-wovens. A tissue paper is defined as a soft absorbent paper having a basis weight below 65 g/m$^2$ and typically between 10 and 50 g/m$^2$. Its density is typically below 0.60 g/cm$^3$, preferably below 0.30 g/cm$^3$ and more preferably between 0.08 and 0.20 g/cm$^3$. Moist tissue paper webs are usually dried against one or more heated rolls. A method, which is commonly used for tissue paper is the so-called Yankee drying. During Yankee drying, the moist paper web is pressed against a steam-heated Yankee cylinder, which can have a very large diameter. The paper web is usually creped against the Yankee cylinder. Another drying method is so called through-air-drying (TAD). In this method the paper is dried by means of hot air blown through the moist paper web, often without a preceding wet pressing. In connection with the TAD drying the patterned structure of the drying fabric is transferred to the paper web. This structure is essentially maintained also in wet condition of the paper, since it has been imparted to the wet paper web.

The tissue produced using the fibre of the invention may be an impulse-dried paper as disclosed in WO 99/34055. Impulse drying shortly involves that the moist paper web is passed through the press nip between a press roll or press shoe and a heated roll, which is heated to such a high temperature that a quick and strong steam generation occurs in the interface between the moist paper web and the heated roll. The resulting paper has a three-dimensional pattern, and a high bulk and softness. The tissue may also be any other type of tissue paper. The tissue paper may be creped or non-creped. The creping may take place in wet or dry condition. It may further be foreshortened by any other methods, such as so called rush transfer between wires.

Apart from cationic fibre's according to the invention, the tissue paper may comprise pulp fibres from chemical pulp, mechanical pulp, thermo-mechanical pulp, chemo-mechanical pulp and/or chemo-thermo-mechanical pulp (CTMP). The fibres may also be recycled fibres. The tissue paper may also contain other types of fibres enhancing e.g. strength, absorption or softness of the paper. Such fibres may be made from regenerated cellulose or synthetic material such as polyolefin, polyesters, polyamides etc.

The tissue paper coming out from the tissue machine as a single-ply paper sheet may be converted to the final tissue product in many ways, for example embossed, laminated to a multi-ply product, rolled or folded. A laminated multi-ply tissue product comprises at least two tissue plies, which are often joined either by an adhesive or mechanically. One or more plies may comprise cationic cellulosic fibres according to the invention. The adhesive may be applied all over the paper or just in regions, for example dots or lines, or only along the edges of the product. The mechanical methods are mainly embossing either over the entire area of the plies or only along the edges, so called edge embossing. In the final product the plies as mostly easy detectable and can often be separated from each other as single plies.

The tissue paper may comprise one or more layers. In the case of more than one layer this is accomplished either in a multi-layered headbox, by forming a new layer on top of an already formed layer or by couching together already formed layers. These layers cannot or only with considerable difficulty be separated from each other and are joined mainly by hydrogen bonds. The different layers may be identical or may have different properties regarding for example fibre composition and chemical composition. One or more layers may comprise cationic cellulosic fibres according to the invention.

The term nonwoven is applied to a wide range of products, which in term of their properties are located between the groups of paper and cardboard on the one hand, and textiles on the other hand. As regards nonwoven a large number of extremely varied production processes are used, such as the air-laid, wetlaid, spunlaced, spunbond, meltblown techniques etc. Nonwovens represent flexible porous fabrics that are not produced by the classical methods of weaving or knitting, but by intertwining and/or by cohesive and/or adhesive bonding of typical synthetic textile fibres, which may for example be present in the form of endless fibres or fibres prefabricated with an endless length, as synthetic fibres produced in situ or in the form of staple fibres. Alternatively they may be made from natural fibres or from blends of synthetic fibres and natural fibres.

One embodiment of the invention provides an absorbent article such as a pant-type diaper, which will effectively enable diapers to lie sealingly against and shape conformingly to the wearer's body, even when the pad is full of liquid. Other absorbent articles in which the cationic fibre of the invention may be incorporated include incontinence devices, sanitary towels, sanitary napkins and the like The cationic fibres according to the invention allow incorporation of a sufficient degree of wet strength in such absorbent articles and especially the absorption pad, while maintaining biodegradability. A pant diaper according to the invention may include an elongated absorbent pad which is enclosed between an inner liquid-permeable casing layer and an outer liquid-impermeable casing layer. The inner casing layer and/or the outer casing layer may comprise cationic cellulosic fibres according to the invention. It is to be understood that it is well within the scope of the invention to put the cationic fibres in distinct layers or mixed with regular cellulosic fibres or polymeric hydrocolloidal material or mixed even with both cellulosic fibres and polymeric hydrocolloidal material. Different combinations with mixed layers and distinct layers are also possible.

EXAMPLES

Example 1

Production of Cationic Fibres and Sheets 60 g pulp (sulphate pulp, TCF, SCA Östrand mill, 370 mmol) was disintegrated and suspended in 6 1 water. Sodium periodate (7.9 g, 37 mmol) was added and the mixture was stirred for 6 days in the dark at pH 5. Then, the sodium iodate was removed by washing the fibres with water. Subsequently, the fibres were resuspended in 2 1 water, Girard's reagent T (trimethylammonioacethydrazide chloride) was added (6.2 g, 37 mmol) and the mixture was stirred for 2 hours at 40° C. The fibres were washed and dewatered as much as possible. The presence of aldehydes in the fibres was shown by reaction with hydroxyl-amine hydrochloride and subsequent release of hydrochloric acid, and the cationic nature was confirmed by the adsorption of polyethylene sodium sulphorate and of MACS (adsorption was followed by polyelectrolyte titration of the supernatant solution containing the anionic polymers).

The cationic fibres were used to make lab sheets (Rapid Köthen). As reference, non modified pulp was used with an addition of 10 kg/t PAE. Sheets were prepared using the cationic fibres and using the cationic fibres with addition of a negatively charged wet strength agent (MACS). As can be seen in the graph of FIG. 1, the sheets obtained with the cationic fibres have wet strength properties comparable with the sheets obtained with non-modified fibres and PAE. Addition of MACS to the cationic fibres gives an improvement of the relative wet strength from 10 to 16%. Note that the strength values for the reference obtained with this sheet former are lower than the ones obtained from a dynamic sheet former (Formette) or from a tissue paper machine. The values for the cationic fibres (with or without MACS) will be proportionally higher.

Example 2

Absorption of Anionic Wet Strength Agent onto Cationic Fibre

Cationic fibres were prepared as described in Example 1. Suspensions of these fibres (100 ml, 1.5% consistency, pH 6.5) were mixed with different amounts of a 1% solution of monoaldehyde carboxy starch (MACS, produced as described in WO 01/83887). The addition levels were 5–50 kg/t and the contact time was 5 minutes. The fibres were filtered through a glass filter and dewatered as much as possible. The non-adsorbed MACS was measured in the filtrate using TOC (total organic carbon analysis). From the values obtained the adsorbed amounts were calculated. The results are shown in the adsorption isotherm shown in FIG. 2. It is shown that 20 kg/t MACS can be adsorbed to the cationic fibres, whereas it was shown that less than 1 kg/t MACS can be absorbed by unmodified fibres (see WO 01/83887).

Example 3
Coupling of 6-Carboxy β-Cyclodextrin to Cationic Fibres

6-Carboxy β-cyclodextrin was prepared by oxidation with 4-acetamido-TEMPO and hypochlorite. Thus, 7.64 g β-cyclodextrin, 150 mg NaBr and 150 mg 4-acetamido-TEMPO in 300 ml water. Sodium hypochlorite was added in doses of 0.20 ml per time. After each dose the reaction was allowed to proceed until no further NaOH consumption was seen. During reaction the pH was kept at 9.3 by addition of NaOH controlled by a pH stat. Two samples were prepared with a degree of oxidation of 0.11 and 0.38, respectively.

Cationic fibres were prepared by oxidation of sulphate pulp fibres (SCA Östrand mill) with sodium periodate (DO= 10%) and the obtained aldehyde groups were subsequently reacted with Girard's reagent T (acethydrazide trimethylammonium chloride). Hereby fibres containing 10% cationic groups were obtained.

Next 30 mg of 6-carboxy β-cyclodextrin (acidic form) was dissolved in 5 ml demineralized water and added to 1g (dry weight) of cationic fibres containing ca. 60% water. The fibres were incubated at 120° C. for about 11 hour. Afterwards the sample was washed with 200 ml de-mineralized water to remove non-adsorbed oxidized cyclodextrin and dried in a fluidized bed dryer for 30 minutes at 60° C.

Example 4
Coupling of Carboxymethylated β-Cyclodextrin to Cationic Fibre

Carboxymethylated β-cyclodextrin was prepared by reaction of β-cyclodextin with mono-chloroacetic acid at pH 12. The product obtained had a degree of substitution of 0.36. The cationic fibres were prepared as described in example 3.

30mg of carboxymethyl β-cyclodextrins were reacted with 1 g cationic fibres (dry weight) as described at example 1, washed with water and dried, as described above.

Example 5
The procedure for the making and characterisation of paper is as follows:
Sheet Making with Derivatives of the Invention
1. Refining TCF pulp is suspended in water (volume 12 litres) and refined to 25 SR° by a Laboratory refiner R1L, Escher Wyss. The consistency of the pulp, when refined, is about 40 g/L so it is diluted to the concentration of 3 g/L.
2. Rapid Köthen Lab-Sheet Former The wet strength additive is added to the pulp suspension and contacted for 2 minutes. Then, the suspension is poured into the lab-sheet former. Sheets are formed according to ISO 5269/2. The sheets are cured for 10 minutes at 105° C.
3. Cutting The sheet is cut into 15 mm strips for testing of dry and wet strength. 100*100 mm is also cut out for measuring the thickness and Grammage.
4. Conditioning The strips are placed in a heating chamber, 105° C. for 10 minutes before testing their wet strength. Then both the strips for wet and dry strength measurement are placed in a climate room, temperature 23° C., moisture 50% for four hours.

5. Grammage and Thickness

100*100 mm pieces of the sheet are used for measuring the Grammage and thickness. Grammage is measured on a regular balance on 4 layers to get an average. Thickness is also measured on four layers and on five different spots to get a good average.
6. Tensile Strength Measurement The strength, both wet and dry, is measured in an Instron SCAN-P58:86. Five 15-mm strips are measured to get an average. When measuring the wet strength, the strip is soaked for 15 sec in tap water.

Example 6
Measuring Binding Ability of Cyclodextrinated Fibres

The binding ability of the modified fibres was determined colorimetrically. 2ml of 20 mg/l phenolphthalein solution in 100 mM $Na_2CO_3$ buffer pH 10.3 was added to 1 g of dry modified fibres. Next the liquid was squeezed out of the fibres and absorption of the solution was measured at 554 nm. The results are summarized in Table 1. The lower the absorption in the squeezed solution is, the more phenolphthalein must have remained bound to the cyclodextrinated fibres. From these results it can be concluded that cyclodextrin derivatives, such as 6-carboxy β-cyclodextrin and carboxymethyl β-cyclodextrin can be bound to fibres and exhibit inclusion properties.

TABLE 1

Phenolphthalein binding capacity of cationic fibres treated with cyclodextrin derivatives and analogues

| Example | description | Absorption at 554 nm |
| --- | --- | --- |
| 6 | cationic fibres (blank) | 0.484 |
| 3 & 6 | 6-carboxy β-cyclodextrin, degree of oxidation (DO) 0.11 | 0.343 |
| 3 & 6 | 6-carboxy β-cyclodextrin, DO 0.38 | 0.314 |
| 4 & 6 | carboxymethyl β-cyclodextrin, DS 0.36 | 0.146 |

We claim:

1. A cationic cellulosic fibre containing between 1 and 30 cationic groups and between 0.1 and 20 aldehyde groups per 100 anhydroglucose units.

2. A cationic cellulosic fibre containing between 1 and 30 cationic groups per 100 anhydroglucose units, obtainable by oxidation of the fibre to introduce aldehyde groups, followed by reaction of aldehyde groups with a nitrogen-containing reagent.

3. A cationic cellulosic fibre containing between 1 and 30 cationic groups per 100 anhydroglucose units, obtainable by reacting the fibre with a nitrogen-containing reagent, followed by oxidation of the fibre to introduce aldehyde groups.

4. A cationic fibre according to claim 1, having a ratio of cationic groups to aldehyde groups of between 1:100 and 1000:1.

5. A paper, tissue or non-woven product comprising a cationic fibre according to claim 1.

6. A paper, tissue or non-woven product according to claim 5, further containing 0.1–10 g of anionic wet strength agent per 100 g of fibre.

7. A paper, tissue or non-woven product according to claim 6, wherein the anionic agent is a carboxylated or oxidized starch derivative.

8. A paper, tissue or non-woven product according to claim 5, which is a multi-ply product.

9. An absorbent article such as a diaper, incontinence device or sanitary towel comprising a cationic cellulosic fibre according to claim 1.

10. A process for producing a cationic fibre, comprising oxidising a cellulosic fibre to introduce aldehyde groups, and reacting at least a part of the aldehyde groups with a nitrogen-containing reagent.

11. A process according to claim 10, wherein the fibre is oxidized with a nitroxyl compound.

12. A process according to claim 10, wherein the fibre is oxidized with periodate.

13. A process according to claim 10, wherein the nitrogen-containing compound is an ammonio-acyl hydrazide.

14. A process for producing a cationic fibre, comprising reacting a cellulosic fibre with a nitrogen-containing reagent and oxidising the fibre to introduce aldehyde groups.

* * * * *